United States Patent [19]

Sato et al.

[11] Patent Number: 5,401,711
[45] Date of Patent: Mar. 28, 1995

[54] PYRIMIDINE DERIVATIVES AND HERBICIDAL COMPOSITION

[75] Inventors: Masahiro Sato; Koichiro Kaku, both of Iwata; Shigehiko Tachikawa, Shizuoka, all of Japan

[73] Assignees: Kumiai Chemical Industry Co., Ltd.; Ihara Chemical Industry Co., Ltd., both of Tokyo, Japan

[21] Appl. No.: 11,908

[22] Filed: Feb. 1, 1993

Related U.S. Application Data

[63] Continuation-in-part of Ser. No. 949,890, Nov. 25, 1992, abandoned.

[30] Foreign Application Priority Data

Jul. 31, 1991 [JP] Japan .................... 3-213085

[51] Int. Cl.⁶ .............. C07D 239/32; C07D 239/47; C07D 239/60; A01N 43/54
[52] U.S. Cl. ....................... 504/242; 504/243; 504/229; 504/193; 544/301; 544/302; 544/312; 544/313; 544/316; 544/317; 544/318
[58] Field of Search ............ 504/242, 243, 193; 544/229, 301, 302, 312, 313, 316, 317, 318

[56] References Cited

U.S. PATENT DOCUMENTS 5,085,686  2/1972  Vogelbacher et al. ............. 504/242
5,167,693  12/1992  Drewes et al. ..................... 504/243
5,201,937  4/1993  Rheinheimer et al. ............. 504/242

FOREIGN PATENT DOCUMENTS 0346789  12/1989  European Pat. Off. .
0490060  6/1992  European Pat. Off. .

OTHER PUBLICATIONS

JP, A, 63-115870 (Kumiai Chemical Industry Co., Ltd), May 20, 1988 (20.05.88).
JP, A, 62-270562 (ICI Australia Ltd.), Nov. 24, 1987 (24.11.87).
JP, A, 62-174059 (Kumiai Chemical Industry Co., Ltd.), Jul. 30, 1987, (30. 07. 87).

Primary Examiner—John M. Ford
Attorney, Agent, or Firm—Oblon, Spivak, McClelland, Maier & Neustadt

[57] ABSTRACT

The present invention provides a herbicidal composition containing a novel pyrimidine derivative having the formula (1),

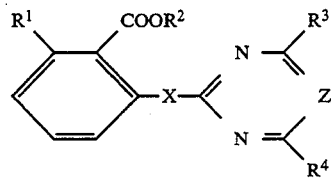

wherein $R^1$ is a trifluoromethanesulfonyloxy group, an ethenyl group which may be substituted, or an ethynyl group which may be substituted; $R^2$ is a hydrogen atom, an alkyl group, 2-trimethylsilyl ethyl group; $R^3$ and $R^4$ are the same or different, and are a methoxy group or a halogen atom; X is an oxygen atom or a sulfur atom; and Z is a methine group; or its salt, as an active ingredient.

The pyrimidine derivative of the present invention exhibits an excellent herbicidal effect against noxious weeds which grow in paddy fields, upland fields and non-agricultural fields.

12 Claims, No Drawings

PYRIMIDINE DERIVATIVES AND HERBICIDAL COMPOSITION

This application is a continuation-in-part application of U.S. patent application Ser. No. 07/949,890, having a filing date of Nov. 25, 1992, now abandoned, which is based on PCT application No. PCT/JP92/00965, filed Jul. 30, 1992, claiming the priority date of Jul. 31, 1991, of Japanese Patent Application No. 213085/1991.

BACKGROUND OF THE INVENTION

1. Field of the Invention

The present invention relates to novel pyrimidine or triazine derivatives and their salts as well as herbicidal compositions containing said pyrimidine or triazine derivatives or their salts which can be applied to paddy fields, upland fields or non-agricultural fields.

2. Discussion of Background

Heretofore, it is known that a compound having the formula,

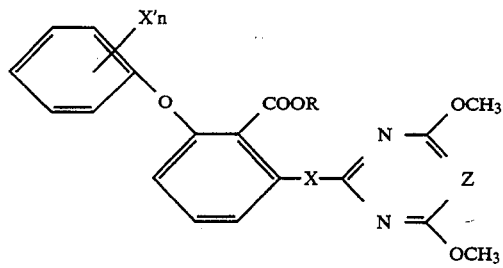

(wherein X' is a halogen atom, a lower alkyl group or lower alkoxy group, R is a hydrogen atom or a benzyl group, and n is an integer of 0, 1 or 2) has a herbicidal activity (Japanese Unexamined Patent Publication No. 250366/1989).

However, the herbicidal effect of the compound disclosed in the above patent publication is not always satisfactory, and a compound achieving a better herbicidal effect is demanded.

We have further studied about pyrimidine or triazine type compounds, aiming at developing a more improved compound. As a result of the study, the present inventors have found that a pyrimidine or triazine derivative having a trifluoromethanesulfonyloxy group, an ethenyl group which may optionally be substituted or an ethynyl group which may optionally be substituted on the benzene ring in place of a phenoxy group, achieves an excellent herbicidal effect on annual and perennial weeds in comparison with the compounds disclosed in the above cited Japanese publication, and have completed the present invention.

SUMMARY OF THE INVENTION

The present invention relates to a pyrimidine or triazine derivative having the formula (1),

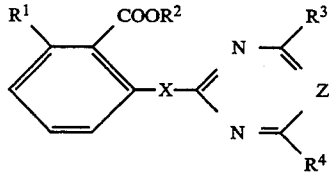

{wherein $R^1$ is a trifluoromethanesulfonyloxy group, a group of the formula,

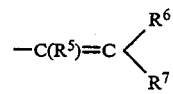

(wherein $R^5$ is a hydrogen atom, a chlorine atom, a lower alkyl group or a lower alkoxy group, $R^6$ is a hydrogen atom, a lower alkyl group, a cyano group or a nitro group, and $R^7$ is a hydrogen atom, a lower alkyl group, a phenyl group, an alkoxycarbonyl group, a haloalkoxycarbonyl group, a phenoxycarbonyl group, a cyano group, a nitro group, a thienyl group, a furyl group or a pyridyl group), a group of the formula $-C\equiv CR^8$ (wherein $R^8$ is a hydrogen atom, a lower alkyl group, a lower alkenyl group, a lower alkoxy group, an alkoxyalkyl group, an alkylthioalkyl group, a phenyl group, a haloalkyl group, a cycloalkyl group, a cycloalkenyl group, a trimethylsilyl group, a cyanoalkyl group, a trifluoromethyl group, an acyloxyalkyl group, or an aminoalkyl group which may be substituted with an alkyl group or a benzyl group) or a group of the formula,

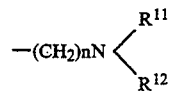

(wherein $R^{11}$ and $R^{12}$ are the same or different, and are a hydrogen atom, a lower alkyl group or a benzyl group, and n is 3 or 4);
$R^2$ is a hydrogen atom, a lower alkyl group, a lower alkenyl group, a lower alkynyl group, a benzyl group, a 2-trimethylsilylethyl group, an alkoxyalkyl group, an alkylthioalkyl group, an alkoxycarbonylalkyl group, a cyanoalkyl group, a nitroalkyl group, or a cation of an alkali metal, an alkali earth metal or an organic amine; $R^3$ and $R^4$ are the same or different, and are a halogen atom, a lower alkyl group, a lower alkoxy group, a difluoromethoxy group, a trifluoromethyl group, or an amino group which may be substituted with a lower alkyl group;
X is an oxygen atom or a sulfur atom; and
Z is a nitrogen atom or a methine group}.

The present invention further relates to a herbicidal composition containing the above-mentioned pyrimidine or triazine derivative or its salt as an active ingredient.

DETAILED DESCRIPTION OF THE INVENTION

In the definition of the formula (1), the alkyl group of a lower alkyl group, an alkoxyalkyl group, an alkylthioalkyl group, a haloalkyl group, a cyanoalkyl group, a nitroalkyl group, an acyloxyalkyl group, or an aminoalkyl group which may be substituted with an alkyl group or a benzyl group, has a carbon number of from 1 to 6; the alkoxy group of a lower alkoxy group, an alkoxyalkyl group, an alkoxycarbonyl group, an alkoxycarbonylalkyl group, or a haloalkoxycarbonyl group, has a carbon number of from 1 to 6; the cycloalkyl group or the cycloalkenyl group has a carbon number of from 3 to 6; and the lower alkenyl group or the lower alkynyl group has a carbon number of from 2 to 6.

Also, in the definition of the formula (1), when illustrating preferable examples of substituents of R², the lower alkyl group is a methyl group, an ethyl group or a propyl group, the lower alkenyl group is an allyl group, the lower alkynyl group is a propargyl group, the alkoxyalkyl group is a methoxymethyl group, the alkylthioalkyl group is a methylthiomethyl group, the alkoxycarbonylalkyl group is a methoxycarbonylmethyl group or a 1-methoxycarbonylethyl group, the cyanoalkyl group is a cyanomethyl group, the nitroalkyl group is a nitromethyl group, the alkali metal is a sodium atom or a potassium atom, the alkaline earth metal is a calcium atom, and the organic amine cation is a diethylammonium cation or a diisopropylammonium cation.

Also, preferable examples of R³ and R⁴ include a chlorine atom as the halogen atom, a methyl group as the lower alkyl group, a methoxy group as the lower alkoxy group, and a dimethylamino group as the amino group which may be substituted with a lower alkyl group. Preferable examples of R⁵ include a methyl group or an ethyl group as the lower alkyl group, and a methoxy group or an ethoxy group as the lower alkoxy group. Preferable examples of R⁶ include a methyl group or an ethyl group as the lower alkyl group. Preferable examples of R⁷ include a chlorine atom as the halogen atom, a methyl group or an ethyl group as the lower alkyl group, and a methoxycarbonyl group, a trifluoroethoxycarbonyl group or a phenoxycarbonyl group as the alkoxycarbonyl group. Preferable examples of R⁸ include a methyl group, an ethyl group, a propyl group or a butyl group as the lower alkyl group, an allyl group as the lower alkenyl group, an ethoxy group as the lower alkoxy group, a methoxymethyl group as the alkoxyalkyl group, a methylthiomethyl group as the alkylthioalkyl group, a chloropropyl group as the haloalkyl group, a cyclopentyl group or a cyclohexyl group as the cycloalkyl group, a 1-cyclohexenyl group as the cycloalkenyl group, a cyanopropyl group as the cyanoalkyl group, and an acetoxymethyl group as the acyloxyalkyl group.

The compounds of the present invention can be produced in accordance with the following processes, but a production process is not limited to these processes.

PROCESS A

As illustrated by the following reaction formula 1, a compound of the formula (1) of the present invention is produced by reacting a compound of the formula (2) with a pyrimidine or triazine compound of the formula (3) in the presence of a base at a temperature preferably in the range of from room temperature to the boiling point of a solvent used.

Reaction formula 1

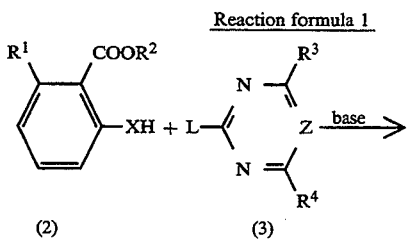

(2)    (3)

-continued
Reaction formula 1

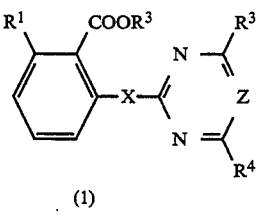

(1)

(wherein R¹, R², R³, R⁴, X and Z are as defined above, and L is a halogen atom, an alkylsulfonyl group, a benzylsulfonyl group or a substituted benzylsulfonyl group.)

Examples of the base used herein, include an alkali metal such as metallic sodium or metallic potassium, a hydrogenated alkali metal and a hydrogenated alkali earth metal such as sodium hydride, potassium hydride or calcium hydride, a carbonate such as sodium carbonate, potassium carbonate or calcium carbonate, a bicarbonate such as sodium hydrogencarbonate or potassium hydrogencarbonate, an alkali metal hydroxide such as sodium hydroxide or potassium hydroxide, an organic acid salt such as potassium acetate, and an alcoholate such as sodium methylate. Also, there can be used an organic base such as pyridine or triethylamine.

Examples of a solvent used, include a hydrocarbon type solvent such as benzene or toluene, a halogenated hydrocarbon type solvent such as ethylene chloride or chloroform, an alcohol type solvent such as ethanol or methanol, an ether type solvent such as ethyl ether, tetrahydrofuran or 1,2-dimethoxyethane, an aprotic polar solvent such as N,N-dimethylformamide, N,N-dimethylacetamide or dimethylsulfoxide, an ester type solvent such as ethyl acetate or methyl acetate, and a ketone type solvent such as acetone or methyl ethyl ketone. When the reaction is conducted in the absence of a solvent, its conditions are not specified, but it is conducted preferably at a temperature in the range of from 120° to 160° C. by using an alkali metal carbonate such as anhydrous potassium carbonate as a base.

PROCESS A-1

Among the compounds of the formula (2), a compound of the formula (5) wherein R¹ is a trifluoromethanesulfonyloxy group and X is an oxygen atom can be produced by reacting a compound of the formula (4) with trifluoromethanesulfonfe anhydride in the presence of a base preferably at a temperature in the range of from −20° C. to 5° C.

Reaction formula 2

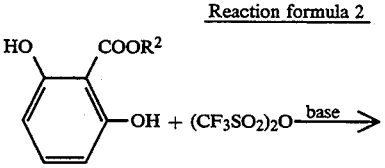

(4)

-continued
Reaction formula 2

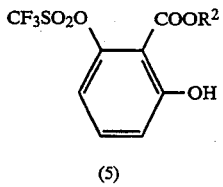

(5)

(wherein $R^2$ is as defined above.)

The same base and the solvent as used in Process A can also be used in the above reaction, but preferable examples of the base include an organic amine such as pyridine, dimethylaminopyridine or triethylamine, a bicarbonate such as sodium hydrogencarbonate or potassium hydrogencarbonate, and a carbonate such as sodium carbonate or potassium carbonate. Preferable examples of the solvent include a halogenated hydrocarbon type solvent such as methylene chloride or chloroform, an ether type solvent such as ethyl ether or tetrahydrofuran, and an aprotic polar solvent such as N,N-dimethylformamide, N,N-dimethylacetamide or dimethylsulfoxide.

PROCESS A-2

Among the compounds of the formula (2), a compound of the formula (8) wherein $R^1$ is a group other than a trifluoromethanesulfonyloxy group and X is an oxygen atom, can be produced by reacting a compound of the formula (6) with a compound of the formula (7) in the presence of a base and a catalyst preferably at a temperature in the range of from room temperature to the boiling point of a solvent.

Reaction formula 3

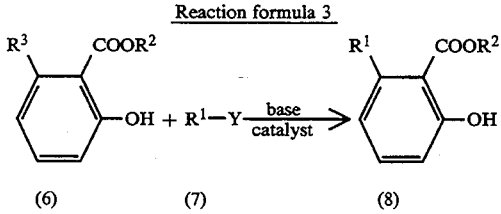

(wherein $R^1$ is a group represented by the formula $-C(R^5)=CR^6CR^7$ or $-C\equiv CR^8$, and $R^2$, $R^5$, $R^6$, $R^7$ and $R^8$ are as defined above. $R^9$ is a halogen atom or a trifluoromethanesulfonyloxy group, and Y is a hydrogen atom or a trialkyl tin group.).

Examples of the catalyst used herein, include tetrakis(triphenylphosphine)palladium(0), bis(triphenylphosphine)palladium dichloride and the like, and other examples include a palladium catalyst such as (palladium acetate, triphenylphosphine) or [palladium acetate, tri(o-tolyl)phosphine]. Examples of the base used herein, include a carbonate such as sodium carbonate or potassium carbonate, a bicarbonate such as sodium hydrogencarbonate, and an organic amine such as triethylamine or pyridine. Examples of the solvent used herein, include a hydrocarbon type solvent such as benzene or toluene, an alcohol type solvent such as ethanol or methanol, an ether type solvent such as ethyl ether, tetrahydrofuran or 1,2-dimethoxyethane, an aprotic polar solvent, such as N,N-dimethylformamide, N,N-dimethylacetamide or dimethylsulfoxide, an ester type solvent such as ethyl acetate, a ketone type solvent such as acetone or methyl ethyl ketone, acetonitrile, and others.

PROCESS A-3

Among the compounds of the formula (2), a compound of the formula (11) wherein $R^1$ is a group of the formula $-CH=CR^6R^7$ and X is an oxygen atom, can be produced by reacting a carbonyl compound with a compound of the formula (9) in the presence of a base preferably at a temperature in the range of from $-78°$ C. to $50°$ C. to prepare a compound of the formula (10) and further reacting the compound of the formula (10) thus prepared, with a demethylating agent preferably at a temperature in the range of from $-78°$ C. to room temperature.

Reaction formula 4

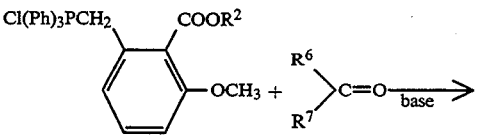

(9)

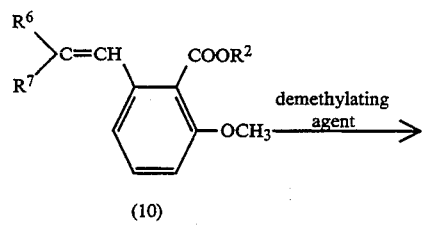

(10)

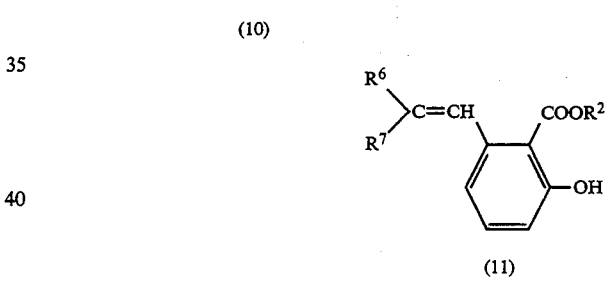

(11)

(wherein $R^2$, $R^6$ and $R^7$ are as-defined above.)

Preferable examples of the base used in the above Wittig reaction, include a lithium reagent such as an alkyl lithium or a lithium bis(trialkylsilyl)amide, an alkali hydride such as sodium hydride, a carbonate such as potassium carbonate, and an alkali metal alkoxide such as potassium tertbutoxide, but sodium amide or others can also be used. Preferable examples of a reagent used as the demethylating agent, include a Lewis acid such as boron tribromide, boron trifluoride, boron trichloride or aluminum chloride, but a hydrogen halide such as hydrogen iodide or hydrogen bromide, trifluoroacetic acid, pyridine hydrochloride, magnesium iodide-ether complex, lithium biphenyl, lithium iodide, sodium thiolate or lithium diphenyl phosphide can also be used.

Examples of the solvent used herein, include a halogen type solvent such as methylene chloride or chloroform, a hydrocarbon type solvent such as hexane, benzene or toluene, an ether type solvent such as ethyl ether or tetrahydrofuran, an aprotic polar solvent such as N,N-dimethylformamide, N,N-dimethylacetamide or dimethoxysulfoxide, an ester type solvent such as ethyl acetate, and an aromatic amine such as collidine, lutidine or pyridine, and other acetonitrile, acetic anhydride or water can also be used.

PROCESS A-4

Among the compounds of the formula (2), a compound of the formula (13) wherein X is a sulfur atom, can be produced by reacting sodium disulfide with a diazonium salt prepared by reacting sodium nitrite with an anthranilic acid derivative of the formula (12) preferably at a temperature of not higher than 10° C.

Reaction formula 5

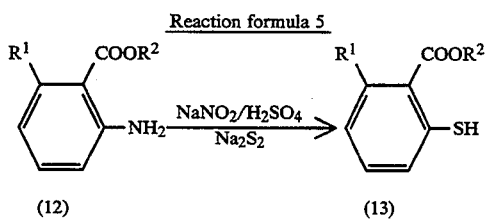

(wherein $R^1$ and $R^2$ are as defined above.)

PROCESS B

A compound of the formula (1) of the present invention can be produced by conducting the following reaction using a compound of the formula (14). The same catalyst, base and solvent as used in the above process A-2 can also be used herein.

Reaction formula 6

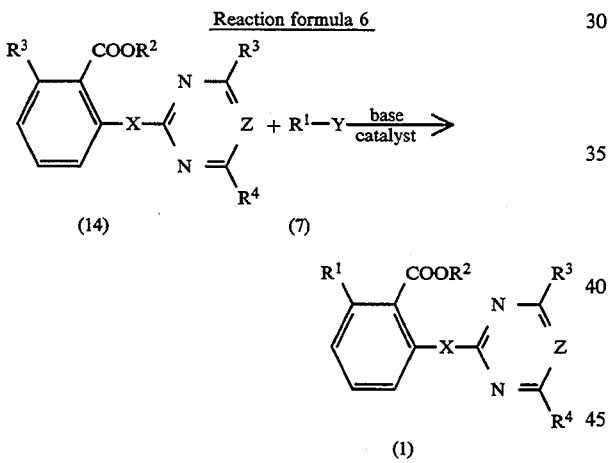

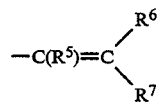

(wherein $R^1$ is a group represented by the formula $$-C(R^5)=C\begin{array}{c}R^6\\ \\R^7\end{array}$$

or the formula $-C\equiv CR^8$; $R^3$ and $R^4$ are the same or different and are a lower alkyl group, a lower alkoxy group, a difludfomethoxy group, a trifluoromethyl group or an amino group which may be substituted with a lower alkyl group; and $R^2$, $R^5$, $R^6$, $R^7$, $R^8$, $R^9$, X, Y and Z are as defined above.)

PROCESS C

Among the compounds of the formula (1) of the present invention, a compound of the formula (16) wherein $R^2$ is a hydrogen atom, can be obtained by hydrolyzing its ester residue. Its process is not specified, but in the present invention, it was produced by reacting a fluorine reagent with a compound of the formula (15) wherein $R^2$ in the formula (1) is a 2-trimethylsilyl ethyl group, preferably at a temperature in the range of from room temperature to the boiling point of a solvent in the following manner.

Reaction formula 7

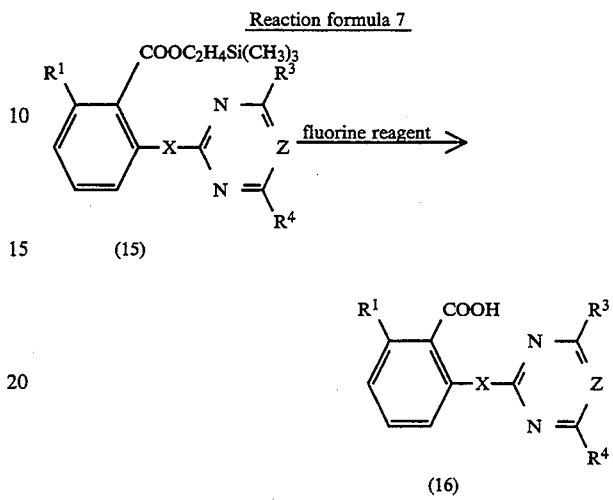

(wherein X, Y, , $R^1$, $R^3$ and $R^4$ are as defined above.)

Preferable examples of the fluorine reagent used herein, include a quaternary ammonium fluoride compound such as tributylammonium fluoride, and an alkali metal fluoride such as potassium fluoride or cesium fluoride. Preferable examples of the solvent used herein, include a hydrocarbon type solvent such as benzene or toluene, a halogenated hydrocarbon type solvent such as methylene chloride or chloroform, an alcohol type solvent such as ethanol or methanol, an ether type solvent such as ethyl ether, tetrahydrofuran or 1,2-dimethoxyethane, an aprotic polar solvent such as N,N-dimethylformamide, N,N-dimethylacetamide or dimethylsulfoxide, an ester type solvent such as ethyl acetate or methyl acetate, and a ketone type solvent such as acetone or methyl ethyl ketone.

PROCESS D

A compound of the formula (17) wherein $R^2$ in the formula (1) is a cation of an alkali metal, an alkaline earth metal or an organic amine, can be produced by reacting a compound of the formula (16) wherein $R^2$ in the formula (1) is a hydrogen atom, which is prepared for example by the above Process C, with a base preferably at a temperature in the range of from room temperature to the boiling point of a solvent.

Reaction formula 8

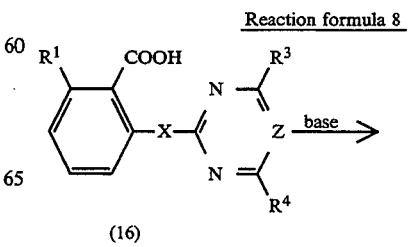

-continued
Reaction formula 8

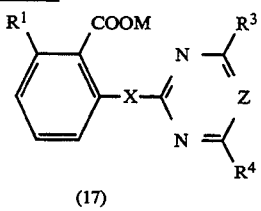

(17)

(wherein $R^1$, $R^3$, $R^4$, X and Y are as defined above M is a cation of an alkali metal such as sodium or potassium, an alkali earth metal such as calcium, or an organic amine.)

Examples of the base used herein, include an alkali metal such as metallic sodium or metallic potassium, a hydrogenated alkali metal or alkali earth metal such as sodium hydride, potassium hydride or calcium hydride, a carbonate such as sodium carbonate, potassium carbonate or calcium carbonate, and an alkali metal hydroxide such as sodium hydroxide or potassium hydroxide. Examples of the organic base include a monoalkylamine such as ammonia or methylamine, a dialkylamine such as dimethylamine, a trialkylamine such as triethylamine, and an aromatic amine such as pyridine.

Examples of the solvent used herein, include water, a hydrocarbon type solvent such as benzene or toluene, a halogenated hydrocarbon type solvent such as methylene chloride or chloroform, an alcohol type solvent such as ethanol or methanol, an ether type solvent such as ethyl ether, tetrahydrofuran, 1,2-dimethoxyethane or 1,4-dioxane, an ester type solvent such as ethyl acetate, a ketone type solvent such as acetone or methyl ethyl ketone, and acetonitrile.

PROCESS E

A compound of the formula (19) wherein $R^2$ in the formula (1) is a lower alkyl group, a lower alkenyl group, a lower alkynyl group, an alkoxyalkyl group, a benzyl group, an alkylthioalkyl group, an alkoxycarbonylalkyl group, a cyanoalkyl group or a nitroalkyl group, can be produced by reacting a compound of the formula (18) with a compound of the formula (16) wherein $R^2$ in the formula (1) is a hydrogen atom, which is prepared for example by Process C, in the presence of an appropriate base preferably at a temperature in the range of from room temperature to the boiling point of a solvent.

Reaction formula 9

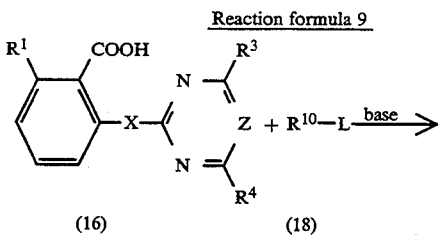

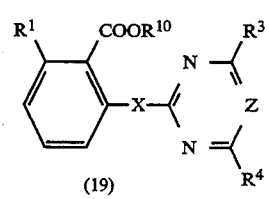

(wherein $R^1$, $R^3$, $R^4$, X, Y and L are as defined above, and $R^{10}$ is a lower alkyl group, a lower alkenyl group, a lower alkynyl group, an alkoxyalkyl group, a benzyl group, an alkylthioalkyl group, a cyanoalkyl group, a nitroalkyl group or an alkoxycarbonylalkyl group.)

Examples of the base used herein, include an alkali metal such as metallic sodium or metallic potassium, a hydrogenated alkali metal such as sodium hydride or potassium hydride, a carbonate such as sodium carbonate or potassium carbonate, a bicarbonate such as sodium hydrogencarbonate or potassium hydrogencarbonate, and an organic amine such as triethylamine, N,N-diisopropylethylamine or pyridine. Examples of the solvent used herein, include a hydrocarbon type solvent such as benzene or toluene, an ether type solvent such as ethyl ether, tetrahydrofuran, 1,2-dimethoxyethane or 1,4-dioxane, an ester type solvent such as ethyl acetate, a ketone type solvent such as acetone or methyl ethyl ketone, a halogen type solvent such as methylene chloride or chloroform, an aprotic polar solvent such as N,N-dimethylformamide, N,N-dimethylacetamide or dimethylsulfoxide, and acetonitrile.

PROCESS F

Among the compounds of the formula (1), a compound of the formula (21) wherein in the formula (1), $R^1$ is an aminoalkyl group, $R^2$ is a hydrogen atom or a methyl group $R^2$ and X is an oxygen atom, can be produced by reducing a compound of the formula (20) wherein in the formula (1), $R^1$ is an aminoalkynyl group and $R^2$ is a benzyl group or a methyl group, with a hydrogen gas in the presence of an appropriate catalyst.

Reaction formula 10

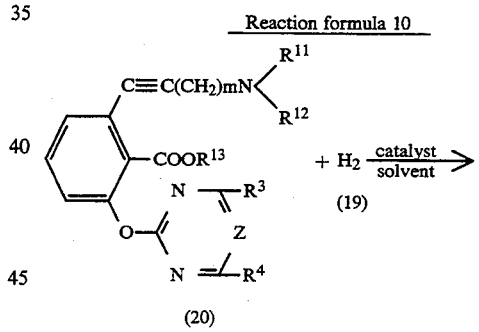

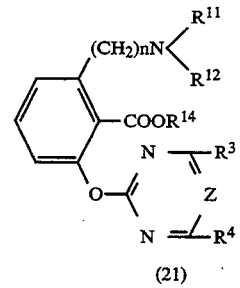

(wherein $R^{13}$ is a methyl group or a benzyl group; $R^{14}$ is a hydrogen atom or a methyl group; m is 1 or 2; and $R^3$, $R^4$, $R^{11}$, $R^{12}$, Z and n are as defined above.)

Examples of the solvent used herein, include a hydrocarbon type solvent such as benzene or toluene, an alcohol type solvent such as methanol or ethanol, an ether type solvent such as ethyl ether, tetrahydrofuran, 1,2-dimethoxyethane or 1,4-dioxane, an ester type solvent such as ethyl acetate, a ketone type solvent such as acetone or methyl ethyl ketone, a halogen type solvent such as methylene chloride or chloroform, an aprotic polar solvent such as N,N-dimethylformamide, N,N-dimethylacetamide or dimethylsulfoxide, water, acetic acid, and formic acid.

Examples of the catalyst include Raney nickel and palladium carbon, but perchloric acid is added only when either of $R^{11}$ or $R^{12}$ contains a benzyl group and the benzyl group is eliminated.

The herbicide of the present invention comprises a pyrimidine or triazine derivative of the formula (1) as an active ingredient.

The compound of the present invention, as a herbicide, may be used as it is or may be formulated in various formulations such as a dust, a wettable powder, an emulsifiable concentrate a fine particle or a granule by blending it with a carrier, a surfactant, a dispersing agent or an adjuvant, which is commonly employed for the formulation of agricultural chemicals.

As the carrier to be used for the formulation, there may be enumerated a solid carrier such as zeeklite, talc, bentonire, clay, kaolin, diatomaceous earth, white carbon, vermiculite, calcium carbonate, slaked lime, silica sand, ammonium sulfate or urea, or a liquid carrier such as isopropyl alcohol, xylene, cyclohexanone, methylnaphthalene or isophorone.

As the surfactant and dispersing agent, there may be enumerated a metal salt of alkylbenzenesulfonic acid, a metal salt of dinaphthylmethanedisulfonic acid, an alcohol-sulfuric acid ester salt, an alkylarylsulfonate, a lignin sulfonate, a polyoxyethylene glycol ether, a polyoxyethylene alkylaryl ether or a polyoxyethylene sorbitol monoalkylate. As the adjuvant, there may be enumerated carboxymethyl cellulose, polyethylene glycol or gum arabic. The herbicide may be diluted to a suitable concentration before application, or may directly be applied.

The herbicide of the present invention is used for foliage treatment, soil treatment or irrigated soil treatment. The proportion of the active ingredient of the present invention in the formulation may optionally vary, but it is usually from 0.01 to 10% by weight, preferably from 0.05 to 5% by weight in the formulation of a dust or a granule. It is generally from 1 to 50% by weight, preferably from 5 to 20% by weight in the formulation of an emulsifiable concentrate or a wettable powder.

The application amount of the herbicide of the present invention may vary depending on the type of a compound used, the type of a weed to be treated, the growing state of weeds, environmental conditions or the type of formulation used, but it is generally from 0.1 g to 5 kg per 10 ares, preferably from 1 g to 1 kg per 10 ares on the basis of the active ingredient in the formulation when it is used as it is, as in the case of a dust or a granule, and it is usually from 0.1 to 50,000 ppm, preferably from 10 to 10,000 ppm when it is used in the state of liquid as in the case of an emulsifiable concentrate or a wettable powder.

If desired, a compound of the present invention may be used in combination with insecticides, sterilizers, other herbicides, plant growth controlling agents, fertilizers or the like.

Now, typical examples of a compound of the formula (1) of the present invention are listed in the following Table 1. Compound numbers are used in the same meanings hereinafter. In the Table, "Ph" represents a phenyl group.

TABLE 1

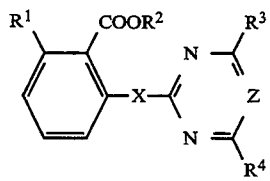

| Compound No. | $R^1$ | $R^2$ | $R^3$ | $R^4$ | X | Y | Melting point (°C.) or Refractive index ($n^{20}$) |
|---|---|---|---|---|---|---|---|
| 1 | CH=CHCH$_3$ | C$_2$H$_4$Si(CH$_3$)$_3$ | OCH$_3$ | OCH$_3$ | O | CH | 1.5341 |
| 2 | CH=CHCH$_3$ | H | OCH$_3$ | OCH$_3$ | O | CH | 80~82 |
| 3 | CH=CHCH$_3$ | CH$_3$ | OCH$_3$ | OCH$_3$ | O | CH | 1.5578 |
| 4 | CH=CHCH$_3$ | C$_2$H$_5$ | OCH$_3$ | OCH$_3$ | O | CH | 65~68.5 |
| 5 | CH=CHCH$_3$ | C$_3$H$_7$ | OCH$_3$ | OCH$_3$ | O | CH | 1.5440 |
| 6 | CH=CHCH$_3$ | C$_3$H$_7$-i | OCH$_3$ | OCH$_3$ | O | CH | 1.5451 |
| 7 | CH=CHCH$_3$ | CH$_2$OCH$_3$ | OCH$_3$ | OCH$_3$ | O | CH | |
| 8 | CH=CHCH$_3$ | CH$_2$CH=CH$_2$ | OCH$_3$ | OCH$_3$ | O | CH | 1.5488 |
| 9 | CH=CHCH$_3$ | CH$_2$C≡CH | OCH$_3$ | OCH$_3$ | O | CH | 108~110 |
| 10 | CH=CHCH$_3$ | CH$_2$PH | OCH$_3$ | OCH$_3$ | O | CH | 1.5699 |
| 11 | CH=CHCH$_3$ | CH$_2$OC$_2$H$_5$ | OCH$_3$ | OCH$_3$ | O | CH | 1.5469 |
| 12 | CH=CHCH$_3$ | CH$_2$CO$_2$CH$_3$ | OCH$_3$ | OCH$_3$ | O | CH | |
| 13 | CH=CHCH$_3$ | CH(CO$_2$CH$_3$)(CH$_3$) | OCH$_3$ | OCH$_3$ | O | CH | 1.5456 |
| 14 | CH=CHCH$_3$ | CH$_2$NO$_2$ | OCH$_3$ | OCH$_3$ | O | CH | |
| 15 | CH=CHCH$_3$ | CH$_2$CN | OCH$_3$ | OCH$_3$ | O | CH | 1.5544 |
| 16 | CH=CHCH$_3$ | CH$_2$SCH$_2$ | OCH$_3$ | OCH$_3$ | O | Cli | 1.5638 |
| 17 | CH=CHCH$_3$ | Na | OCH$_3$ | OCH$_3$ | O | CH | 223~228 |
| 18 | CH=CHCH$_3$ | ½-Ca | OCH$_3$ | OCH$_3$ | O | CH | |

TABLE 1-continued

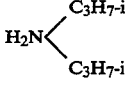

| Compound No. | R¹ | R² | R³ | R⁴ | X | Y | Melting point (°C.) or Refractive index ($n^{20}$) |
|---|---|---|---|---|---|---|---|
| 19 | CH=CHCH₃ | H₂N\<C₃H₇-i / C₃H₇-i | OCH₃ | OCH₃ | O | CH | 121~135 |
| 20 | CH=CHCH₃ | C₂H₄Si(CH₃)₃ | OCH₃ | OCH₃ | S | CH | |
| 21 | CH=CHCH₃ | H | OCH₃ | OCH₃ | S | CH | 145~147 |
| 22 | CH=CHCH₃ | C₂H₄Si(CH₃)₃ | Cl | OCH₃ | O | CH | |
| 23 | CH=CHCH₃ | H | Cl | OCH₃ | O | CH | |
| 24 | CH=CHCH₃ | C₂H₄Si(CH₃)₃ | CF₃ | OCH₃ | O | CH | 1.5029 |
| 25 | CH=CHCH₃ | H | CF₃ | OCH₃ | O | CH | 132~137 |
| 26 | CH=CHCH₃ | C₂H₄Si(CH₃)₃ | N(CH₃)₂ | OCH₃ | O | CH | |
| 27 | CH=CHCH₃ | H | N(CH₃)₂ | OCH₃ | O | CH | |
| 28 | CH=CHCH₃ | C₂H₄Si(CH₃)₃ | CH₃ | CH₃ | O | CH | 1.5342 |
| 29 | CH=CHCH₃ | H | CH₃ | CH₃ | O | CH | 135~139 |
| 30 | CH=CHCH₃ | C₂H₄Si(CH₃)₃ | OCH₃ | OCH₃ | O | N | 1.5295 |
| 31 | CH=CHCH₃ | H | OCH₃ | OCH₃ | O | N | 112~115 |
| 32 | CH=CHCH₃ | CH₃ | OCH₃ | OCH₃ | O | N | Unmeasurable |
| 33 | CH=CHPh | C₂H₄Si(CH₃)₃ | OCH₃ | OCH₃ | O | CH | 1.5375 |
| 34 | CH=CHPh | H | OCH₃ | OCH₃ | O | CH | 134~136 |
| 35 | CH=CHCO₂CH₃ | C₂H₄Si(CH₃)₃ | OCH₃ | OCH₃ | O | CH | 1.5392 |
| 36 | CH=CHCO₂CH₃ | H | OCH₃ | OCH₃ | O | CH | 95~98 |
| 37 | C≡CSi(CH₃)₃ | C₂H₄Si(CH₃)₃ | OCH₃ | OCH₃ | O | CH | 1.5285 |
| 38 | C≡CH | C₂H₄Si(CH₃)₃ | OCH₃ | OCH₃ | O | CH | 1.5342 |
| 39 | C≡CH | H₂N\<C₃H₇-i / C₃H₇-i | OCH₃ | OCH₃ | O | CH | |
| 40 | OSO₂CF₃ | C₂H₄Si(CH₃)₃ | OCH₃ | OCH₃ | O | CH | 1.4951 |
| 41 | CH=CH₃ | C₂H₄Si(CH₃)₃ | OCH₃ | OCH₃ | O | CH | 1.5310 |
| 42 | CH=CH₃ | H | OCH₃ | OCH₃ | O | CH | 112~117 |
| 43 | C≡C—CH₂N\<CH₃ / CH₃ | C₂H₄Si(CH₃)₃ | OCH₃ | OCH₃ | O | CH | 1.5351 |
| 44 | C≡C—CH₂N\<CH₃ / CH₃ | H₂N\<C₃H₇-i / C₃H₇-i | OCH₃ | OCH₃ | O | CH | |
| 45 | C≡C—Ph | C₂H₄Si(CH₃)₃ | OCH₃ | OCH₃ | O | CH | Unmeasurable |
| 46 | C≡C—Ph | H₂N\<C₂H₅)₂ | OCH₃ | OCH₃ | O | CH | 107~116 |
| 47 | C≡C—C₄H₅ | C₂H₄Si(CH₃)₃ | OCH₃ | OCH₃ | O | CH | 1.5322 |
| 48 | C≡C—C₄H₅ | H₂N\<C₃H₇-i / C₃H₇-i | OCH₃ | OCH₃ | O | CH | |
| 49 | C≡C—C₄H₅-t | C₂H₄Si(CH₃)₃ | OCH₃ | OCH₃ | O | CH | 1.5312 |
| 50 | C≡C—C₄H₃-t | H₂N\<C₃H₇-i / C₃H₇-i | OCH₃ | OCH₃ | O | CH | 122~127 |
| 51 | C≡C—C₄H₃-t | CH₃ | OCH₃ | OCH₃ | O | CH | 1.5375 |
| 52 | C≡C—C₃H₇ | C₂H₄Si(CH₃)₃ | OCH₃ | OCH₃ | O | CH | 1.5339 |

TABLE 1-continued

Structure: R¹ and COOR² on benzene ring; X connects to C(=N-C(R³)=Z-C(R⁴)=N) ring system with Y.

| Compound No. | R¹ | R² | R³ | R⁴ | X | Y | Melting point (°C.) or Refractive index (n²⁰) |
|---|---|---|---|---|---|---|---|
| 53 | C≡C—C₃H₇ | H₂N(C₃H₇-i)(C₃H₇-i) | OCH₃ | OCH₃ | O | CH | 125~131 |
| 54 | C≡C—C₃H₇ | CH₃ | OCH₃ | OCH₃ | O | CH | 1.5339 |
| 55 | C(=CH₂)OC₂H₅ | C₂H₄Si(CH₃)₃ | OCH₃ | OCH₃ | O | CH | 1.5330 |
| 56 | C(=CH₂)OC₂H₅ | H | OCH₃ | OCH₃ | O | CH | |
| 57 | C≡C—C₃H₆Cl | C₂H₄Si(CH₃)₃ | OCH₃ | OCH₃ | O | CH | 1.5446 |
| 58 | C≡C—C₃H₆Cl | H₂N(C₃H₇-i)(C₃H₇-i) | OCH₃ | OCH₃ | O | CH | 133~137 |
| 59 | C≡C—C₃H₆Cl | CH₃ | OCH₃ | OCH₃ | O | CH | 1.5634 |
| 60 | C≡C—CH₃ | C₂H₄Si(CH₃)₃ | OCH₃ | OCH₃ | O | CH | 1.5356 |
| 61 | C≡C—CH₃ | H₂N(C₃H₇-i)(C₃H₇-i) | OCH₃ | OCH₃ | O | CH | |
| 62 | C≡C—CH₃ | CH₃ | OCH₃ | OCH₃ | O | CH | |
| 63 | C≡C—C₂H₅ | C₂H₄Si(CH₃)₃ | OCH₃ | OCH₃ | O | CH | Unmeasurable |
| 64 | C≡C—C₂H₅ | H₂N(C₃H₇-i)(C₃H₇-i) | OCH₃ | OCH₃ | O | CH | 126~129.5 |
| 65 | C≡C—C₂H₅ | CH₃ | OCH₃ | OCH₃ | O | CH | |
| 66 | CH=CH-(2-thienyl) | C₂H₄Si(CH₃)₃ | OCH₃ | OCH₃ | O | CH | 1.5795 |
| 67 | CH=CH-(2-thienyl) | H | OCH₃ | OCH₃ | O | CH | 142~146 |
| 68 | CH=CH-(2-thienyl) | CH₃ | OCH₃ | OCH₃ | O | CH | |
| 69 | CH=CH-(2-pyridyl) | C₂H₄Si(CH₃)₃ | OCH₃ | OCH₃ | O | CH | |

TABLE 1-continued

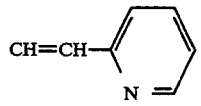

| Compound No. | R¹ | R² | R³ | R⁴ | X | Y | Melting point (°C.) or Refractive index ($n^{20}$) |
|---|---|---|---|---|---|---|---|
| 70 | 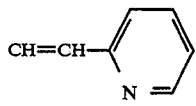 | H | OCH$_3$ | OCH$_3$ | O | CH | |
| 71 | 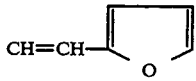 | CH$_3$ | OCH$_3$ | OCH$_3$ | O | CH | |
| 72 | 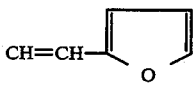 | C$_2$H$_4$Si(CH$_3$)$_3$ | OCH$_3$ | OCH$_3$ | O | CH | |
| 73 | 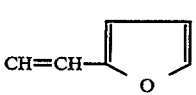 | H | OCH$_3$ | OCH$_3$ | O | CH | |
| 74 |  | CH$_3$ | OCH$_3$ | OCH$_3$ | O | CH | |
| 75 |  | C$_2$H$_4$Si(CH$_3$)$_3$ | OCH$_3$ | OCH$_3$ | O | CH | |
| 76 | 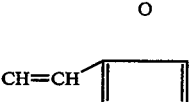 | H | OCH$_3$ | OCH$_3$ | O | CH | |
| 77 | 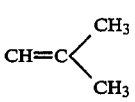 | CH$_3$ | OCH$_3$ | OCH$_3$ | O | CH | |
| 78 | 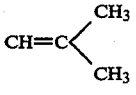 | C$_2$H$_4$Si(CH$_3$)$_3$ | OCH$_3$ | OCH$_3$ | O | CH | 1.5232 |
| 79 | 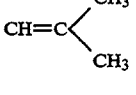 | H | OCH$_3$ | OCH$_3$ | O | CH | Unmeasurable |
| 80 | 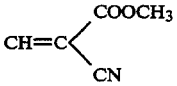 | CH$_3$ | OCH$_3$ | OCH$_3$ | O | CH | |
| 81 | CH=C(COOCH$_3$)(CN) | C$_2$H$_4$Si(CH$_3$)$_3$ | OCH$_3$ | OCH$_3$ | O | CH | |

TABLE 1-continued $$\text{structure with } R^1, COOR^2, R^3, R^4, X, Z, N, Y$$

| Compound No. | $R^1$ | $R^2$ | $R^3$ | $R^4$ | X | Y | Melting point (°C.) or Refractive index ($n^{20}$) |
|---|---|---|---|---|---|---|---|
| 82 | CH=C(COOCH$_3$)(CN) | H | OCH$_3$ | OCH$_3$ | O | CH | |
| 83 | CH=CHCN(E) | C$_2$H$_4$Si(CH$_3$)$_3$ | OCH$_3$ | OCH$_3$ | O | CH | 1.5430 |
| 84 | CH=CHCN(E) | H | OCH$_3$ | OCH$_3$ | O | CH | 129~133 |
| 85 | CH=CHCN(Z) | C$_2$H$_4$Si(CH$_3$)$_3$ | OCH$_3$ | OCH$_3$ | O | CH | 1.5329 |
| 86 | CH=CHCN(Z) | H | OCH$_3$ | OCH$_3$ | O | CH | 165~170 |
| 87 | CH=C(COOCH$_3$)(NO$_2$) | C$_2$H$_4$Si(CH$_3$)$_3$ | OCH$_3$ | OCH$_3$ | O | CH | |
| 88 | CH=C(COOCH$_3$)(NO$_2$) | H | OCH$_3$ | OCH$_3$ | O | CH | |
| 89 | CH=CHNO$_2$ | C$_2$H$_4$Si(CH$_3$)$_3$ | OCH$_3$ | OCH$_3$ | O | CH | |
| 90 | CH=CHNO$_2$ | H | OCH$_3$ | OCH$_3$ | O | CH | |
| 91 | CCl=CH$_2$ | C$_2$H$_4$Si(CH$_3$)$_3$ | OOCH$_3$ | OCH$_3$ | O | CH | |
| 92 | CCl=CH$_2$ | H | OCH$_3$ | OCH$_3$ | O | CH | |
| 93 | C≡C-cyclohexyl | C$_2$H$_4$Si(CH$_3$)$_3$ | OCH$_3$ | OCH$_3$ | O | CH | 1.5485 |
| 94 | C≡C-cyclohexyl | H$_2$N(C$_3$H$_7$-i)(C$_3$H$_7$-i) | OCH$_3$ | OCH$_3$ | O | CH | 82~103 |
| 95 | C≡C-cyclohexyl | CH$_3$ | OCH$_3$ | OCH$_3$ | O | CH | |
| 96 | C≡C-OC$_2$H$_5$ | C$_2$H$_4$Si(CH$_3$)$_3$ | OCH$_3$ | OCH$_3$ | O | CH | |
| 97 | C≡C-OC$_2$H$_5$ | H$_2$N(C$_3$H$_7$-i)(C$_3$H$_7$-i) | OCH$_3$ | OCH$_3$ | O | CH | |
| 98 | C≡C-OC$_2$H$_5$ | CH$_3$ | OCH$_3$ | OCH$_3$ | O | CH | |
| 99 | C≡C-cyclohexenyl | C$_2$H$_4$Si(CH$_3$)$_3$ | OCH$_3$ | OCH$_3$ | O | CH | |
| 100 | C≡C-cyclohexenyl | H$_2$N(C$_3$H$_7$-i)(C$_3$H$_7$-i) | OCH$_3$ | OCH$_3$ | O | CH | |

TABLE 1-continued $$R^1 \text{-benzene ring with } COOR^2, X\text{-}C(=N\text{-}CR^3)\text{-}Z\text{-}N=CR^4 \text{ triazine-like structure}$$

| Compound No. | $R^1$ | $R^2$ | $R^3$ | $R^4$ | X | Y | Melting point (°C.) or Refractive index ($n^{20}$) |
|---|---|---|---|---|---|---|---|
| 101 | C≡C-(1-cyclohexenyl) | $CH_3$ | $OCH_3$ | $OCH_3$ | O | CH | |
| 102 | C≡C-$CH_2CH_2CH_2CN$ | $C_2H_4Si(CH_3)_3$ | $OCH_3$ | $OCH_3$ | O | CH | 1.5360 |
| 103 | C≡C-$CH_2CH_2CH_2CN$ | $H_2N\langle{}^{C_3H_7\text{-}i}_{C_3H_7\text{-}i}$ | $OCH_3$ | $OCH_3$ | O | CH | 130~136 |
| 104 | C≡C-$CH_2CH_2CH_2CN$ | $CH_3$ | $OCH_3$ | $OCH_3$ | O | CH | Unmeasurable |
| 105 | C≡C-$CH_2OCH_3$ | $C_2H_4Si(CH_3)_3$ | $OCH_3$ | $OCH_3$ | O | CH | |
| 106 | C≡C-$CH_2OCH_3$ | $H_2N\langle{}^{C_3H_7\text{-}i}_{C_3H_7\text{-}i}$ | $OCH_3$ | $OCH_3$ | O | CH | |
| 107 | C≡C-$CH_2OCH_3$ | $CH_3$ | $OCH_3$ | $OCH_3$ | O | CH | |
| 108 | C≡C-C(CH$_3$)=CH$_2$ | $C_2H_4Si(CH_3)_3$ | $OCH_3$ | $OCH_3$ | O | CH | |
| 109 | C≡C-C(CH$_3$)=CH$_2$ | $H_2N\langle{}^{C_3H_7\text{-}i}_{C_3H_7\text{-}i}$ | $OCH_3$ | $OCH_3$ | O | CH | |
| 110 | C≡C-C(CH$_3$)=CH$_2$ | $CH_3$ | $OCH_3$ | $OCH_3$ | O | CH | |
| 111 | C≡C-cyclopentyl | $C_2H_4Si(CH_3)_3$ | $OCH_3$ | $OCH_3$ | O | CH | Unmeasurable |
| 112 | C≡C-cyclopentyl | $H_2N\langle{}^{C_3H_7\text{-}i}_{C_3H_7\text{-}i}$ | $OCH_3$ | $OCH_3$ | O | CH | 131~137 |
| 113 | C≡C-cyclopentyl | $CH_3$ | $OCH_3$ | $OCH_3$ | O | CH | |
| 114 | C≡C-$CH_2SCH_3$ | $C_2H_4Si(CH_3)_3$ | $OCH_3$ | $OCH_3$ | O | CH | |
| 115 | C≡C-$CH_2SCH_3$ | $H_2N\langle{}^{C_3H_7\text{-}i}_{C_3H_7\text{-}i}$ | $OCH_3$ | $OCH_3$ | O | CH | |
| 116 | C≡C-$CH_2SCH_3$ | $CH_3$ | $OCH_3$ | $OCH_3$ | O | CH | |
| 117 | C≡C-$CF_3$ | $C_2H_4Si(CH_3)_3$ | $OCH_3$ | $OCH_3$ | O | CH | |

TABLE 1-continued

Structure: R¹ and COOR² on benzene ring, with X connecting to C(=N-)(N=) center bearing R³ and R⁴ groups with Z (Y).

| Compound No. | R¹ | R² | R³ | R⁴ | X | Y | Melting point (°C.) or Refractive index ($n^{20}$) |
|---|---|---|---|---|---|---|---|
| 118 | C≡C—CF₃ | $H_2N\!\!<\!\!{}^{C_3H_7\text{-}i}_{C_3H_7\text{-}i}$ | OCH₃ | OCH₃ | O | CH | |
| 119 | C≡C—CF₃ | CH₃ | OCH₃ | OCH₃ | O | CH | |
| 120 | C≡C—CH₂OCOCH₃ | C₂H₄Si(CH₃)₃ | OCH₃ | OCH., | O | CH | |
| 121 | C≡C—CH₂OCOCH₃ | $H_2N\!\!<\!\!{}^{C_3H_7\text{-}i}_{C_3H_7\text{-}i}$ | OCH₃ | OCH₃ | O | CH | |
| 122 | C≡C—CH₂OCOCH₃ | CH₃ | OCH₃ | OCH₃ | O | CH | |
| 123 | C≡C—CH₂CH=CH₂ | C₂H₄Si(CH₃)₃ | OCH₃ | OCH₃ | O | CH | |
| 124 | C≡C—CH₂CH=CH₂ | $H_2N\!\!<\!\!{}^{C_3H_7\text{-}i}_{C_3H_7\text{-}i}$ | OCH₃ | OCH₃ | O | CH | |
| 125 | C≡C—CH₂CH=CH₂ | CH₃ | OCH₃ | OCH₃ | O | CH | |
| 126 | CH=CHCO₂CH₂CF₃ | C₂H₄Si(CH₃)₃ | OCH₃ | OCH₃ | O | CH | 1.4925 |
| 127 | CH=CHCO₂CH₂CF₃ | H | OCH₃ | OCH₃ | O | CH | |
| 128 | CH=CHCO₂C₆H₅ | C₂H₄Si(CH₃)₃ | OCH₃ | OCH₃ | O | CH | |
| 129 | CH=CHCO₂C₆H₅ | H | OCH₃ | OCH₃ | O | CH | |
| 130 | C(CH₃)=CHCO₂CH₃ | C₂H₄Si(CH₃)₃ | OCH₃ | OCH₃ | O | CH | |
| 131 | C(CH₃)=CHCO₂CH₃ | H | OCH₃ | OCH₃ | O | CH | |
| 132 | CH=C(COOC₄H₉-t)(CH₃) | C₂H₄Si(CH₃)₃ | OCH₃ | OCH₃ | O | CH | 1.5132 |
| 133 | CH=C(COOC₄H₉-t)(CH₃) | H | OCH₃ | OCH₃ | O | CH | Unmeasurable |
| 134 | CH=C(COOC₄H₉-t)(CH₃) | CH₂OCH₃ | OCH₃ | OCH₃ | O | CH | 1.5223 |
| 135 | CH=C(COOCH₃)(CH₃) | H | OCH₃ | OCH₃ | O | CH | Unmeasurable |
| 136 | CH=CHCH₃ | C₂H₄Si(CH₃)₃ | OCHF₂ | OCH₃ | O | CH | 1.5215 |
| 137 | CH=CHCH₃ | H | OCHF₂ | OCH₃ | O | CH | 1.5189 |
| 138 | CH=CHCOOH | H | OCH₃ | OCH₃ | O | CH | 154~160 |
| 139 | CH=CHCH₂CH₃ | H | OCH | OCH | O | CH | 1.5591 |
| 140 | OSO₂CF₃ | CH₂Ph | OCH₃ | OCH₃ | O | CH | 1.5319 |
| 141 | OSO₂CF₃ | H | OCH₃ | OCH₃ | O | CH | 1.34-136 |
| 142 | C≡C—CH₂N(CH₃)₂ | CH₂Ph | OCH₃ | OCH₃ | O | CH | Unmeasurable |

TABLE 1-continued

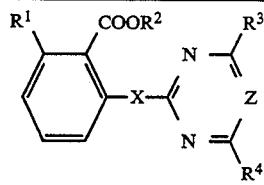

| Compound No. | R¹ | R² | R³ | R⁴ | X | Y | Melting point (°C.) or Refractive index ($n^{20}$) |
|---|---|---|---|---|---|---|---|
| 143 | CH₂CH₂CH₂N(CH₃)₂ | H | OCH₃ | OCH₃ | O | CH | 205–208 |
| 144 | CH₂CH₂CH₂N(CH₃)₂ | CH₃ | OCH₃ | OCH₃ | O | CH | |
| 145 | C≡C—CH₂N(C₂H₅)₂ | CH₂Ph | OCH₃ | OCH₃ | O | CH | |
| 146 | CH₂CH₂CH₂N(C₂H₅)₂ | H | OCH₃ | OCH₃ | O | CH | |
| 147 | CH₂CH₂CH₂N(C₂H₅)₂ | CH₃ | OCH₃ | OCH₃ | O | CH | |
| 148 | C≡C—CH₂N(CH₃)(CH₂Ph) | CH₂Ph | OCH₃ | OCH₃ | O | CH | |
| 149 | CH₂CH₂CH₂N(CH₃)(CH₂Ph) | H | OCH₃ | OCH₃ | O | CH | |
| 150 | CH₂CH₂CH₂N(CH₃)(CH₂Ph) | CH₃ | OCH₃ | OCH₃ | O | CH | |
| 151 | CH₂CH₂CH₂NHCH₂Ph | H | OCH₃ | OCH₃ | O | CH | |
| 152 | C(=CH₂)OCH₃ | CH₂Ph | OCH₃ | OCH₃ | O | CH | |
| 153 | C(=CH₂)OCH₃ | H | OCH₃ | OCH₃ | O | CH | |

Now, the present invention will be described in further detail with reference to Examples. However, it should be understood that the present invention is by no means restricted to such specific Examples.

EXAMPLE 1

Preparation of 2-trimethylsilylethyl 2-[(4,6-dimethoxypyrimidin-2-yl)oxy]-6-(1-propenyl)benzoate (Compound No. 1)

In a 50 ml round bottom-flask, there were charged 2-trimethylsilylethyl 6-(1-propenyl)salicylate (3.1 g, 11.0 mmol), 4,6-dimethoxy-2-methylsulfonylpyrimidine (2.4 g, 11.0 mmol), potassium carbonate (1.8 g, 13.0 mmol) and 10 ml of N,N-dimethylformamide (hereinafter referred to as "DMF"), and the resultant mixture was reacted for 1 hour at 80° C. After cooling the reaction mixture, DMF was distilled off under reduced pressure, and the residue thus obtained was dissolved in ethyl acetate, washed with water and a saturated salt water, dried with anhydrous sodium sulfate and concentrated. The resultant residue was purified by silica gel column chromatography to obtain 2.0 g (yield:

47.6%) of the aimed product (colorless transparent viscous liquid).

EXAMPLE 2

Preparation of 2-[(4,6-dimethoxypyrimidin-2-yl)oxy]-6-(1-propenyl)benzoic acid (Compound No. 2)

(2-Trimethylsilyl)ethyl 2-[(4,6-dimethoxypyrimidin-2-yl)oxy]-6-(1-propenyl)benzoate (2.0 g, 5.0 mmol) was dissolved in tetrahydrofuran (20 ml, hereinafter referred to as "THF") in a 50 ml round bottom-flask, and tetrabutylammonium fluoride hydrate (3.5 g, 13.3 mmol) was added thereto little by little. The resultant mixture was stirred at room temperature for 2 hours, and THF was distilled off under reduced pressure. To the residue thus obtained, was added water, and the resultant mixture was adjusted to pH 3 with 10% hydrochloric acid and was then extracted with ethyl acetate. The resultant product was then washed with water and a saturated salt water, dried with anhydrous sodium sulfate and concentrated. The residue thus obtained was washed with hexane, and the solvent was completely distilled off to obtain 1.0 g (yield: 66.7%)-of the aimed product (red-brown glass-like material).

EXAMPLE 3

Preparation of 2-trimethylsilylethyl 2-[(4,6-dimethoxypyrimidin-2-yl)oxy]-6-vinylbenzoate (Compound No. 41)

In a 100 ml flask equipped with a thermometer, a cooling tube and a nitrogen-introducing tube, there were charged 2-trimethylsilylethyl 2-[(4,6-dimethoxypyrimidin-2-yl)oxy]-6-trifluoromethylsulfonyloxybenzoate (3.15 g, 6.0 mmol), tetrakis(triphenylphosphine)palladium(0) (400 mg, 0.34 mmol) and toluene (30 ml), and the resultant mixture was stirred at room temperature for 1 hour under nitrogen stream. After adding 2,6-di-tert-butyl-4-methylphenol (catalytic amount) to the resultant mixture, vinyl tributyl tin (3.17 g, 10.0 mmol) was further added and the mixture was reacted at 80°–90° C. for 3 hours. After cooling the mixture, toluene was added thereto and the organic layer was washed with water and a saturated salt water, dried with anhydrous sodium sulfate and concentrated. The residue thus obtained was purified by silica gel column chromatography to obtain 0.50 g (yield: 20.8%) of the aimed product (transparent viscous orange color liquid).

EXAMPLE 4

Preparation of 2-trimethylsilylethyl 2-[(4,6-dimethoxypyrimidin-2-yl)oxy]-6-(1-pentynyl)benzoate (Compound No. 52)

In a 100 ml flask equipped with a thermometer, a cooling tube and a nitrogensintroducing tube, there were charged 2-trimethylsilylethyl 2-[(4,6-dimethoxypyrimidin-2-yl)oxy]-6-trifluoromethylsulfonyloxybenzoate (4.72 g, 9.0 mmol), bis(triphenylphosphine)palladium dichloride (300 mg, 0.4 mmol), DMF (30 ml) and triethylamine (5 ml), and the resultant mixture was stirred at room temperature for 1 hour under nitrogen stream. Thereafter, 1-pentyne (2.0 g, 29.40 mmol) was added to the resultant mixture, and the mixture was reacted at 80°–90° C. for 3 hours. After cooling, the mixture was poured into an ice water, and was extracted with ethyl acetate. The organic layer thus obtained was washed with water and a saturated salt water, dried with anhydrous sodium sulfate and concentrated. The residue thus obtained was then purified by silica gel column chromatography to obtain 2.50 g (yield: 62.8%) of the aimed product (red-brown transparent viscous liquid).

EXAMPLE 5

Preparation of diisopropylammonium 2-[(4,6-dimethoxypyrimidin-2-yl)oxy]-6-(1-pentynyl)benzoate (Compound No. 53)

In a 100 ml round bottom-flask, there was charged 2-trimethylsilylethyl 2-[(4,6-dimethoxypyrimidin-2-yl)oxy]-6-(1-pentynyl)benzoate (2.10 g, 4.7 mmol) dissolved in THF (50 ml), and tetrabutylammonium fluoride hydrate (1 mol-THF solution, 14.2 ml, 14.2 mmol) was added thereto. The resultant mixture was stirred at room temperature for 3 hours. After distilling off THF under reduced pressure, water was added thereto, and the mixture was adjusted to pH 3 with 10% hydrochloric acid and was extracted with ethyl acetate. The organic layer thus obtained was washed with water and a saturated salt water, and dried with anhydrous sodium sulfate and concentrated. The resultant residue thus obtained was added to methanol (50 ml) having diisopropylamine (1.01 g, 10.0 mmol) dissolved, and the resultant mixture was stirred at 50° C. for 2 hours. After cooling, the solvent was distilled off, and the resultant product was recrystallized with isopropylether to obtain 1.74 g (yield: 83.7%) of the aimed product (light yellowish granular crystal).

EXAMPLE 6

Preparation of methyl 2-[(4,6-dimethoxypyrimidin-2-yl)oxy]-6-(1-pentynyl)benzoate (Compound No. 54)

Diisopropylammonium 2-[(4,6-dimethoxypyrimidin-2-yl)oxy]-6-(1-pentynyl)benzoate (1.00 g, 2.3 mmol) was dissolved in tetrahydrofuran (20 ml)-DMF (10 ml) in a 50 ml round bottom-flask, and methyl iodide (1.4 g, 10.0 mmol) was added thereto little by little. The resultant mixture was stirred at 50° C. for 2 hours and THF-DMF was distilled off under reduced pressure. Water was added to the resultant residue, and the residue was extracted with ethyl acetate. The organic layer thus obtained was washed with water and a saturated salt water, dried with anhydrous sodium sulfate and concentrated. To the resultant mixture, was added an appropriate amount of Florisil, and the mixture was eluted with ispropyl ether. The solvent was then distilled off under reduced pressure to obtain 0.61 g (yield: 76.3 %) of the aimed product (yellow viscous liquid).

EXAMPLE 7

Preparation of methyl 2-[(4,6-dimethoxypyrimidin-2-yl)-oxy-6-(3-dimethylaminopropyl)benzoate (Compound No. 144)

In a 100 ml round bottom-flask, there were charged benzyl 2-[(4,6-dimethoxypyrimidin-2-yl)oxy]-6-(3-dimethylamino-1-propynyl)benzoate (1.60 g, 3.6 mmol), 10% palladium carbon (0.2 g) and methanol (50 ml), and hydrogen gas was introduced therein. After confirming that a required amount of hydrogen was consumed, palladium carbon was filtrated out, and methanol was distilled off under reduced pressure. The residue thus obtained was purified by column chromatography using Florisil to obtain 0.50 g (yield: 38.8%) of the aimed product (yellow-brown powder).

Now, typical Formulation Examples for a herbicidal composition of the present invention will be given. However, it should be understood that the present invention is by no means restricted to these specific Formulation Examples, and the type of a compound, the type of an additive and the blending ratio may be widely varied. In these Examples, "part" means part by "weight".

FORMULATION EXAMPLE 1

(Wettable powder)

10 Parts of Compound No. 64, 0.5 part of polyoxyethylene octylphenyl ether, 0.5 part of a sodium salt of β-naphthalenesulfonic acid-formalin condensate, 20 parts of diatomaceous earth and 69 parts of clay were mixed and pulverized to obtain a wettable powder.

FORMULATION EXAMPLE 2

(Wettable powder)

10 Parts of Compound No. 58, 0.5 part of polyoxyethylene octyl phenyl ether, 0.5 part of a sodium salt of β-naphthalenesulfonic acid-formalin condensate, 20 parts of diatomaceous earth, 5 parts of white carbon and 64 parts of clay were mixed and pulverized to obtain a wettable powder.

FORMULATION EXAMPLE 3

(Wettable powder containing calcium carbonate)

10 Parts of Compound No. 18, 0.5 part of a sodium salt of β-naphthalenesulfonic acid-formalin condensate, 0.5 part of a mixture of sodium laurylsulfate and sodium sulfate, 20 parts of diatomaceous earth, 5 parts of white carbon and 64 parts of calcium carbonate were mixed and pulverized to obtain a wettable powder.

FORMULATION EXAMPLE 4

(Emulsifiable concentrate)

30 Parts of Compound No. 38, 60 parts of an equivalent mixture of xylene and isophorone, and 10 parts of a mixture of polyoxyethylene sorbitan alkylate, polyoxyethylene alkylaryl polymer and alkylaryl sulfonate, were fully mixed to obtain an emulsifiable concentrate.

FORMULATION EXAMPLE 5

(Granule)

3 Parts of Compound No. 2, 87 parts of a bulking agent comprising a ½ mixture of talc/bentonite, 5 parts of white carbon, 5 parts of a surfactant mixture of polyoxyethylene sorbitan alkylate, polyoxyethylene alkylaryl polymer and alkylaryl sulfonate, and 10 parts of water, were fully kneaded to obtain a paste-like material. The paste-like material was then extruded to a sieve aperture of 0.7 mm in diameter, and the extruded product was dried and cut into pieces of 0.5 to 1 mm in length to obtain granules.

Now, the effect of a compound of the present invention will be described with reference to Test Examples.

TEST EXAMPLE 1

(herbicidal effect test by paddy field soil treatment)

In a plastic pot filled with paddy field soil (surface area: 100 cm$^2$), seeds of barnyardgrass (Ec), monochoria (Mo) and bulrush (Sc) were sown after puddling and leveling, and water was flooded thereon to a depth of 3 cm. Next day, a wettable powder prepared in accordance with Formulation Example 1 was diluted with water, and was applied dropwise to the pot in an amount of 100 g/10 a as an active ingredient. Then, the pot was cultured in a green house, and evaluation was conducted on the 21st day after the treatment in accordance with the standard as identified in the following Table 2. The results are shown in the following Table 3.

TABLE 2

| Index No. | Herbicidal effects (degree of growth control) |
| --- | --- |
| 5 | Herbicidal effect: at least 90% control |
| 4 | Herbicidal effect: at least 70% and less than 90% |
| 3 | Herbicidal effect: at least 50% and less than 70% |
| 2 | Herbicidal effect: at least 30% and less than 50% |
| 1 | Herbicidal effect: at least 10% and less than 30% |
| 0 | Herbicidal effect: at least 0% and less than 10% |

TABLE 3

| Compound No. | Herbicidal effect | | |
| --- | --- | --- | --- |
| | Ec | Mo | Sc |
| 2 | 5 | 5 | 5 |
| 11 | 5 | 5 | 5 |
| 13 | 5 | 5 | 5 |
| 21 | 5 | 5 | 5 |
| 34 | 5 | 5 | 5 |
| 36 | 4 | 5 | 5 |
| 37 | 5 | 5 | 5 |
| 38 | 5 | 5 | 5 |
| 42 | 5 | 5 | 5 |
| 46 | 5 | 5 | 5 |
| 50 | 5 | 5 | 5 |
| 53 | 5 | 5 | 5 |
| 54 | 5 | 5 | 5 |
| 55 | 5 | 5 | 5 |
| 58 | 5 | 5 | 5 |
| 59 | 5 | 5 | 5 |
| 60 | 5 | 5 | 5 |
| 63 | 5 | 5 | 5 |
| 64 | 5 | 5 | 5 |
| 79 | 5 | 5 | 5 |
| 112 | 5 | 5 | 5 |
| 137 | 5 | 5 | 5 |
| 139 | 5 | 5 | 5 |

TEST EXAMPLE 2

(herbicidal effect test by upland field soil treatment)

In a plastic pot filled with upland field soil (surface area: 120 cm$^2$), seeds of edible barnyardgrass (Ec), pale smartweed (Po), slender amaranth (Am), lambsquarters (Ch) and rice flatsedge (Ci) were sown and covered with soil. A predetermined amount of a wettable powder prepared in accordance with Formulation Example 1 was diluted with water and applied uniformly to the soil surface by a small-sized sprayer in an amount of 100 1/10 a so that the dose of the active ingredient was 100 g/10 a. The pot was then cultured in a green house, and evaluation was conducted on the 21st day after the treatment in accordance with the standard as identified in the following Table 2. The test results are shown in the following Table 4.

TABLE 4

| Compound No. | Herbicidal effect | | | | |
| --- | --- | --- | --- | --- | --- |
| | Ec | Po | Am | Ch | Ci |
| 2 | 5 | 5 | 5 | 5 | 5 |
| 11 | 5 | 5 | 5 | 5 | 5 |
| 13 | 3 | 5 | 5 | 5 | 4 |
| 15 | 5 | 5 | 5 | 5 | 5 |
| 21 | 5 | 5 | 5 | 5 | 5 |
| 34 | 3 | 4 | 5 | 5 | 5 |

TABLE 4-continued

| Compound No. | Herbicidal effect | | | | |
|---|---|---|---|---|---|
| | Ec | Po | Am | Ch | Ci |
| 36 | 4 | 5 | 5 | 5 | 5 |
| 37 | 3 | 5 | 5 | 5 | 5 |
| 38 | 4 | 5 | 5 | 5 | 5 |
| 42 | 5 | 5 | 5 | 5 | 5 |
| 46 | 4 | 5 | 5 | 5 | 5 |
| 50 | 4 | 5 | 5 | 5 | 5 |
| 53 | 5 | 5 | 5 | 5 | 5 |
| 54 | 3 | 5 | 5 | 5 | 3 |
| 58 | 5 | 5 | 5 | 5 | 5 |
| 59 | 4 | 5 | 5 | 5 | 5 |
| 60 | 5 | 5 | 5 | 5 | 5 |
| 63 | 3 | 5 | 5 | 5 | 5 |
| 67 | 3 | 5 | 5 | 5 | 4 |
| 79 | 5 | 5 | 5 | 5 | 5 |
| 112 | 5 | 5 | 5 | 5 | 5 |
| 137 | 4 | 5 | 5 | 5 | 5 |
| 139 | 5 | 5 | 5 | 5 | 5 |
| 141 | 2 | 5 | 5 | 5 | 5 |

TEST EXAMPLE 3

(herbicidal effect test by upland field foliage treatment)

In a plastic pot filled with upland soil (surface area: 120 cm²), seeds of edible barnyardgrass (Ec), pale smartweed (Po), slender amaranth (Am), lambsquarters (Ch) and rice flatsedge (Ci) were sown, and were cultured in a green house for 2 weeks. A predetermined amount of a wettable powder prepared in accordance with Formulation Example 1 was diluted with water, and applied by a small-sized sprayer onto the foliage in an amount of 100 l/10 a so that the dose of the active ingredient was 100 g/10 a. The plants were cultured in a green house, and evaluation was conducted on the 14th day after the treatment in accordance with the standard as identified in the following Table 2. The test results are shown in the following Table 5.

TABLE 5

| Compound No. | Herbicidal effect | | | | |
|---|---|---|---|---|---|
| | Ec | Po | Am | Ch | Ci |
| 2 | 5 | 5 | 5 | 5 | 5 |
| 11 | 5 | 5 | 5 | 5 | 5 |
| 13 | 4 | 5 | 5 | 5 | 5 |
| 15 | 5 | 5 | 5 | 5 | 5 |
| 21 | 5 | 5 | 5 | 5 | 5 |
| 34 | 5 | 5 | 5 | 5 | 5 |
| 36 | 4 | 5 | 5 | 5 | 5 |
| 37 | 4 | 5 | 5 | 5 | 5 |
| 38 | 5 | 5 | 5 | 5 | 5 |
| 42 | 5 | 5 | 5 | 5 | 5 |
| 46 | 5 | 5 | 5 | 5 | 5 |
| 50 | 4 | 5 | 5 | 3 | 3 |
| 53 | 5 | 5 | 5 | 5 | 5 |
| 57 | 3 | 5 | 5 | 5 | 3 |
| 58 | 5 | 5 | 5 | 5 | 5 |
| 59 | 5 | 5 | 5 | 5 | 5 |
| 60 | 4 | 5 | 5 | 5 | 5 |
| 63 | 3 | 5 | 5 | 4 | 5 |
| 64 | 5 | 5 | 5 | 5 | 5 |
| 67 | 5 | 5 | 5 | 5 | 5 |
| 79 | 5 | 5 | 5 | 5 | 5 |
| 112 | 5 | 5 | 5 | 5 | 5 |
| 137 | 5 | 5 | 5 | 5 | 5 |
| 139 | 5 | 5 | 5 | 5 | 5 |
| 141 | 2 | 5 | 5 | 4 | 3 |

What is claimed is:

1. A pyrimidine derivative having the formula,

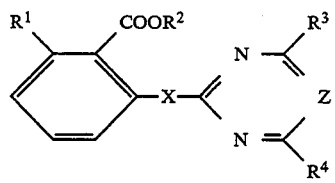

wherein $R^1$ is (1) a trifluoromethylsulfonyloxy group;
(2) a group of the formula,

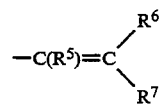

wherein $R^5$ is a hydrogen atom, a lower alkyl group or a lower alkoxy group, $R^6$ is a hydrogen atom, a lower alkyl group, a cyano group or a nitro group, and $R^7$ is a hydrogen atom, a lower alkyl group, a phenyl group, an alkoxycarbonyl group, a haloalkoxycarbonyl group, a phenoxycarbonyl group, a cyano group, a nitro group, a thienyl group, a furyl group or a pyridyl group, with the proviso that $R^5$, $R^6$ and $R^7$ can not all be hydrogen and with the proviso that none of groups $R^5$, $R^6$ and $R^7$ can be methyl;

(3) a group of the formula [—C≡CR$^8$] —C≡CR$^8$, wherein $R^8$ is a lower alkyl group, with the proviso that $R^8$ can not be methyl, a lower alkenyl group, a lower alkoxy group, an alkoxyalkyl group, an alkylthioalkyl group, a phenyl group, a haloalkyl group, a cycloalkyl group, a cycloalkenyl group, a trimethylsilyl group, a cyanoalkyl group, a trifluoromethyl group, an acyloxyalkyl group, or an aminoalkyl group which may be substituted with an alkyl group or a benzyl group; or (4) a group of the formula,

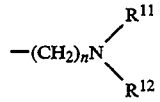

wherein $R^{11}$ and $R^{12}$ are the same or different, and are a hydrogen atom, a lower alkyl group or a benzyl group, and n is 3 or 4;

$R^2$ is a hydrogen atom, a lower alkyl group, a lower alkenyl group, a lower alkynyl group, a benzyl group, a 2-trimethylsilylethyl group, an alkoxyalkyl group, an alkylthioalkyl group, an alkoxycarbonylalkyl group, a cyanoalkyl group, a nitroalkyl group, or a cation of an alkali metal, an alkaline earth metal or an organic amine;

$R^3$ and $R^4$ are the same or different, and are a halogen atom, a lower alkyl group, a lower alkoxy group, a difluoromethoxy group, a trifluoromethyl group, or an amino group which may be substituted with a lower alkyl group;

X is an oxygen atom or a sulfur atom; and z is a roethine group, or its salt.

2. The pyrimidine derivative or its salt according to claim 1, wherein R' is a trifluoromethylsulfonyloxy group.

3. The pyrimidine derivative or its salt according to claim 1, wherein R' is a group of the formula,

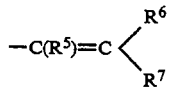

(wherein $R^5$ is a hydrogen atom, a lower alkyl group or a lower alkoxy group, $R^6$ is a hydrogen atom, a lower alkyl group, a cyano group or a nitro group, and $R^7$ is a hydrogen atom, a lower alkyl group, a phenyl group, an alkoxycarbonyl group, a haloalkoxycarbonyl group, a phenoxycarbonyl group, a cyano group, a nitro group, a thienyl group, a furyl group or a pyridyl group).

4. The pyrimidine derivative or its salt according to claim 1, wherein R' is a group of the formula —C≡CR$^8$ (wherein $R^8$ is a lower alkyl group, a lower alkenyl group, a lower alkoxy group, an alkoxyalkyl group, an alkylthioalkyl group, a phenyl group, a haloalkyl group, a cycloalkyl group, a cycloalkenyl group, a trimethylsilyl group, a cyanoalkyl group, a trifluoromethyl group, an acyloxyalkyl group, or an aminoalkyl group which may be substituted with an alkyl group or a benzyl group).

5. The pyrimidine derivative or its salt according to claim 1, wherein R' is a group of the formula,

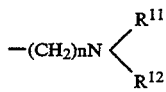

(wherein $R^{11}$ and $R^{12}$ are the same or different, and are a hydrogen atom, a lower alkyl group or a benzyl group, and n is 3 or 4).

6. The pyrimidine derivative or its salt according to any of claims 1, 2, 3, 4 or 5, wherein $R^2$ is a methyl group, an ethyl group, a propyl group, an allyl group, a propargyl group, a methoxymethyl group, a methylthiomethyl group, a methoxycarbonylmethyl group, a 1-methoxycarbonylethyl group, a cyanomethyl group, a nitromethyl group, a sodium atom, a potassium atom, a calcium atom, a diethylammonium cation or a diisopropylammonium cation; $R^3$ and $R^4$ are a halogen atom, a methyl group, a methoxy group or a dimethylamino group; $R^5$ is a methyl group, an ethyl group, a methoxy group or an ethoxy group; $R^6$ is a methyl group or an ethyl group; $R^7$ is a halogen atom, a methyl group, an ethyl group, a methoxycarbonyl group, a trifluoroethoxycarbonyl group or a phenoxycarbonyl group; and $R^8$ is a methyl group, an ethyl group, a propyl group, a butyl group, an allyl group, an ethoxy group, a methoxymethyl group, a methylthiomethyl group, a chloropropyl group, a cyclopentyl group, a cyclohexyl group, a 1-cyclohexenyl group, a cyanopropyl group or an acetoxymethyl group.

7. The pyrimidine derivative or its salt according to claim 1, wherein X is an oxygen atom.

8. The pyrimidine derivative or its salt according to claim 2, wherein X is an oxygen atom.

9. The pyrimidine derivative or its salt according to claim 3, wherein X is an oxygen atom.

10. The pyrimidine derivative or its salt according to claim 4, wherein X is an oxygen atom.

11. The pyrimidine derivative or its salt according to claim 5, wherein X is an oxygen atom.

12. A herbicidal composition comprising:
  a herbicidally effective amount of the pyrimidine compound of claim 1 and an agriculturally acceptable carrier.

* * * * *